(12) United States Patent
Nicolas et al.

(10) Patent No.: US 12,110,378 B2
(45) Date of Patent: *Oct. 8, 2024

(54) METHOD FOR DEPOSITING NANO-OBJECTS ON THE SURFACE OF A POLYMER GEL WITH UNIFORM RIGIDITY

(71) Applicants: Centre national de la recherche scientifique, Paris (FR); UNIVERSITE GRENOBLE ALPES, Saint Martin d'Heres (FR); Commissariat à l'énergie atomique et aux énergies alternatives, Paris (FR)

(72) Inventors: Alice Nicolas, Grenoble (FR); Camille Migdal, Grenoble (FR)

(73) Assignees: Centre National De La Recherche Scientifique, Paris (FR); Universite Grenoble Alpes, Saint Martin d'Heres (FR); Commissariat À L'énergie Atomique Et Aux Énergies Alternatives, Paris (FR)

( * ) Notice: Subject to any disclaimer, the term of this patent is extended or adjusted under 35 U.S.C. 154(b) by 1060 days.

This patent is subject to a terminal disclaimer.

(21) Appl. No.: 16/980,025

(22) PCT Filed: Mar. 12, 2019

(86) PCT No.: PCT/EP2019/056168
§ 371 (c)(1),
(2) Date: Sep. 11, 2020

(87) PCT Pub. No.: WO2019/175177
PCT Pub. Date: Sep. 19, 2019

(65) Prior Publication Data
US 2021/0009782 A1    Jan. 14, 2021

(30) Foreign Application Priority Data
Mar. 12, 2018   (FR) .................................. 18 52101

(51) Int. Cl.
*C08J 9/36* (2006.01)
*B81C 1/00* (2006.01)
(Continued)

(52) U.S. Cl.
CPC ............. *C08J 9/36* (2013.01); *B81C 1/00206* (2013.01); *C08J 7/04* (2013.01); *C08J 9/365* (2013.01);
(Continued)

(58) Field of Classification Search
CPC ..... B81C 1/00206; B82Y 30/00; B82Y 40/00; C08J 2205/022; C08J 2205/042;
(Continued)

(56) References Cited

U.S. PATENT DOCUMENTS 10,286,101 B2   5/2019   Leibler et al.
11,383,004 B2   7/2022   Leibler et al.
(Continued)

FOREIGN PATENT DOCUMENTS

CN   107033513 A   8/2017
CN   107189294 A   9/2017
JP   2006272002    10/2006

OTHER PUBLICATIONS

Tse, et al., "Preparation of Hydrogel Substrates with Tunable Mechanical Properties", Jun. 2010, pp. 10.16.1-10.16.16, Supplement 47, Current Protocols in Cell Biology.
(Continued)

*Primary Examiner* — Lynda Salvatore
(74) *Attorney, Agent, or Firm* — B. Aaron Schulman, Esq.; Stites & Harbison, PLLC

(57) ABSTRACT

The invention relates to a method for depositing nano-objects on the surface of a gel comprising the steps of: a) providing a gel having a polymer matrix and a solvent within the polymer matrix, the polymer matrix forming a three-
(Continued)

dimensional network which is capable of swelling in the presence of the solvent, wherein the solubility of the polymer matrix in the solvent at 1 bar and 25° C. is less than 1 g/l, wherein the gel has a rigidity gradient on the micrometer scale of less than 10%, then b) depositing nano-objects on the surface of the gel, the nano-objects having a mean diameter greater than or equal to the mean diameter of the pores of the gel, then c) evaporating the solvent from the gel at least until the content of solvent no longer varies over time, under the proviso that, at the start of evaporation, the content of mineral salts in the solvent is less than 6 g/l, the gel capable of being obtained and the uses thereof.

10 Claims, 2 Drawing Sheets

(51) Int. Cl.
| | |
|---|---|
| *B82Y 30/00* | (2011.01) |
| *B82Y 40/00* | (2011.01) |
| *C08J 7/04* | (2020.01) |
| *C12N 11/089* | (2020.01) |
| *C12N 11/098* | (2020.01) |

(52) U.S. Cl.
CPC .......... *C12N 11/089* (2020.01); *C12N 11/098* (2020.01); *B82Y 30/00* (2013.01); *B82Y 40/00* (2013.01); *C08J 2205/022* (2013.01); *C08J 2205/042* (2013.01); *C08J 2205/10* (2013.01); *C08J 2333/26* (2013.01); *C08J 2389/00* (2013.01)

(58) Field of Classification Search
CPC ............... C08J 2205/10; C08J 2301/00; C08J 2333/26; C08J 2371/02; C08J 2383/04; C08J 2389/00; C08J 7/04; C08J 9/0028; C08J 9/36; C08J 9/365
See application file for complete search history.

(56) References Cited

U.S. PATENT DOCUMENTS

| | | | |
|---|---|---|---|
| 2016/0002368 A1* | 1/2016 | Gulino | G03F 7/20 |
| | | | 430/269 |
| 2016/0215171 A1 | 7/2016 | Marcellan et al. | |
| 2016/0325010 A1* | 11/2016 | Liebler | A61L 24/08 |
| 2019/0275195 A1 | 9/2019 | Leibler et al. | |
| 2021/0002450 A1* | 1/2021 | Nicolas | C08J 3/28 |

OTHER PUBLICATIONS

Preliminary Search Report for FR 1852101 dated Nov. 23, 2018.
Saha, et al., "Surface Creasing Instability of Soft Polyacrylamide Cell Culture Substrates", Biophysical Journal, vol. 99, Dec. 2010, pp. L94-L96.
International Search Report dated May 13, 2019 in International Application No. PCT/EP2019/056168.
Zaari N et al, "Photopolymerization in Microfluidic Gradient Generators: Microscale Control of Substrate Compliance to Manipulate Cell Response", Dec. 1, 2004, pp. 2133-2137, vol. 16, No. 23-24, Advanced Materials, Wiley-VCH Germany, DE, XP002679866.

* cited by examiner

METHOD FOR DEPOSITING NANO-OBJECTS ON THE SURFACE OF A POLYMER GEL WITH UNIFORM RIGIDITY

The present invention relates to a method for depositing nano-objects on the surface of a polymer gel with uniform rigidity, the gel the gel capable of being obtained and its applications.

In many fields, in particular in biology, pharmaceuticals, or diagnostics, devices comprising a substrate whose surface comprises nano-objects (proteins, nanoparticles, etc.) are sought after.

It is relatively easy to deposit nano-objects on the surface of a "hard" substrate such as glass or silicon. However, in order to strengthen the bonding forces between the surface and the nano-objects and thus to extend the life of the device, it is desired to replace glass or silicon with softer substrates, such as gels based on a polymer matrix, such as hydrogels.

The density of a gel based on a polymer matrix is directly related to its porosity. The more porous a gel, the less rigid it is, and vice versa.

Controlling the surface density of nano-objects deposited on the surface of gels is an issue in the field of cell culture, where we wish to cultivate cells on the surface of substrates of physiological rigidity (of the order of kPa), while preserving quantitative control of the surface chemistry. This need is particularly pressing for stem cell engineering and is emerging in the field of pharmacological screening. Cells adapt their biochemical responses to the rigidity of their environment in addition to adapting them to their chemical environment, so there is a need to independently control the rigidity and chemical properties of in vitro cell culture media and implantable media.

The methods of depositing nano-objects on the surface of existing gels depend on the chemical structure of the gel. More precisely, three techniques are used.

According to a first technique, the monomers used to prepare the polymer of the polymer matrix are modified to include the nano-object. In this case, control of the surface density of the polymer obtained is possible, but the surface density of nano-objects obtained on the gel is directly linked to the rigidity/porosity of the gel.

The other two techniques are based on depositing and then grafting nano-objects on the surface of the totally or partially solvated gel:
- a solution of nano-objects is brought into contact with the gel, the surface of which has been optionally activated beforehand (by grafting a reaction intermediate and/or by radiation); or
- the nano-objects are modified to make them reactive with the surface of the gel and then added in the form of a solution to the surface of the gel.

In these two cases, the surface density of grafted nano-objects is dependent on the porosity/rigidity of the gel as soon as the method includes a partial drying step, which is generally unavoidable, for example when removing the solution of nano-objects to carry out the grafting reaction of nano-objects. In fact, the gels are porous materials, and therefore very sensitive to dehydration: the characteristic drying times are generally of the order of a few seconds (typically for a gel with a rigidity of the order of 0.1 kPa) to a few minutes (typically for a gel with a rigidity of the order of 25 kPa) depending on the porosity/rigidity of the gel. On the other hand, if the gel is kept completely solvated during the method, the surface density of deposited nano-objects is independent of the rigidity/porosity of the gel. However, the deposition efficiency of nano-objects is very low given the low probability of the nano-objects approaching and interacting with the gel surface, as these two techniques are limited by the diffusion of the nano-objects towards the surface. Thus, these two techniques do not make it possible to easily control the surface density of deposited nano-objects.

There is therefore a need to develop a method for depositing nano-objects on the surface of a gel which makes it possible to control the surface density of deposited nano-objects, without it depending on the rigidity of the gel.

To this end, according to a first object, the invention relates to a method for depositing nano-objects on the surface of a gel comprising the steps of:
a) providing a gel comprising a polymer matrix and a solvent within the polymer matrix, the polymer matrix forming a three-dimensional network capable of swelling in the presence of said solvent, where the solubility of the polymer matrix at 1 bar and 25° C. in the solvent is less than 1 g/l, where the gel exhibits a variability in rigidity at the micrometer scale of less than 10%, then
b) depositing nano-objects on the surface of the gel, said nano-objects having an average diameter greater than or equal to the average diameter of the pores of the gel, then
c) evaporating the solvent from the gel at least until the solvent content no longer varies with time, provided that at the start of evaporation, the content of inorganic salts in the solvent is less than 6 g/l.

The method comprises a step a) of providing a gel comprising a polymer matrix and a solvent within the polymer matrix, the polymer matrix forming a three-dimensional network capable of swelling in the presence of said solvent, where the solubility of the polymer matrix at 1 bar and 25° C. in the solvent is less than 1 g/l.

The gel comprises a polymer matrix and a solvent within the polymer matrix, the polymer matrix forming a three-dimensional network capable of swelling in the presence of said solvent. The polymer matrix is therefore capable of retaining a proportion of solvent within its structure. Generally, the maximum solvent content within the polymer matrix of the gel at 25° C. (calculated as the ratio of the maximum solvent weight to the sum of the maximum solvent weight and the weight of the dry polymer matrix) varies from 20 to 100%, preferably from 38 to 100%. When we continue to add solvent beyond the maximum content, the added solvent is no longer incorporated into the polymer matrix.

The polymer of the polymer matrix of the gel may be homopolymeric (three-dimensional network formed from a homopolymer), copolymeric (three-dimensional network formed from a copolymer) or multipolymeric (three-dimensional Interpenetrating Polymer Network (IPN)).

Generally, the polymer matrix comprises (or even consists of) a polymer chosen from among:
- polyacrylamides;
- polyethylene glycols, polypropylene glycols and ethylene glycol or propylene glycol copolymers, these optionally comprising units resulting from the polymerization of (meth)acrylate compounds;
- polysaccharides, optionally comprising repeating units resulting from the polymerization of (meth)acrylate compounds;
- (co)polymers resulting from the polymerization of diacrylate and/or (meth)acrylate compounds;
- polyvinyl alcohols comprising repeating units resulting from the polymerization of (meth)acrylate compounds;

dextrans comprising repeating units resulting from the polymerization of (meth)acrylate compounds;

polypropylene fumarates and poly (propylene fumarate-co-ethylene glycol);

polysiloxanes, such as poly(dimethylsiloxane) (PDMS); and the combinations of these.

Polymer matrices based on polyacrylamides, and, in particular, resulting from the polymerization of acrylamide and N,N'-methylenebisacrylamide, are particularly preferred.

The term "(meth)acrylate compounds" is understood to mean compounds derived from acrylate or methacrylate, for example chosen from among acrylic acid (AA), methacrylic acid (MA), ethylene glycol dimethacrylate (EGDMA), 2-hydroxyethyl methacrylate (HEMA), sulfopropyl acrylate, where the acids may be in the form of a salt, in particular sodium or potassium.

The solvent may be any solvent in which the solubility of the polymer matrix at 1 bar and 25° C. is less than 1 g/L and in which it is capable of swelling.

For example, the solvent may be an aqueous solution or an organic solvent chosen from among alcohols, alkanes (pentane, hexane for example), amines (triethylamine, diisopropylamine for example), ketones (acetone for example), and aromatic solvents (toluene, xylene for example).

In one embodiment, the polymer matrix comprises (or even consists of) polysiloxanes, such as poly(dimethylsiloxane) (PDMS), while the solvent is chosen from among pentane, triethylamine, diisopropylamine or xylene.

The most common solvent is an aqueous solution, and is preferably water, optionally deionized. The gel is then a hydrogel. Examples of hydrogels are found in the review by Enas M. Ahmed (Journal of Advanced Research, 2015, 6, 105-121). The polymer matrix then generally comprises (or even consists of) a polymer chosen from among:

polyacrylamides, for example resulting from the polymerization of acrylamide and N, N'-methylenebisacrylamide;

polyethylene glycols, polypropylene glycols and ethylene glycol or propylene glycol copolymers, these optionally comprising units resulting from the polymerization of (meth)acrylate compounds;

polysaccharides, optionally comprising repeating units resulting from the polymerization of (meth)acrylate compounds);

(co)polymers resulting from the polymerization of diacrylate and/or (meth)acrylate compounds;

polyvinyl alcohols comprising repeating units resulting from the polymerization of (meth)acrylate compounds;

dextrans comprising repeating units resulting from the polymerization of (meth)acrylate compounds;

polypropylene fumarates and poly(propylene fumarate-co-ethylene glycol); and the combinations of these.

The rigidity of the gel provided in step a) is uniform. In the gel provided in step a), the standard deviation a of the rigidity values Ri (where i varies from 1 to n) is preferably less than 20%, typically less than 15%, in particular less than 10%, especially less than 5%, preferably less than 1%, the rigidity values Ri being measured by atomic force microscopy on n points distributed over the entire surface of the gel provided in step a), n being greater than 50, typically greater than 100, in particular greater than 1,000, preferably greater than 10,000, the standard deviation a being as defined in formula (I):

$$\sigma = \sqrt{\frac{1}{n}\sum_{i=1}^{n}(Ri - \text{mean})^2} \quad \text{(I)}$$

where "mean" is the arithmetic mean of the rigidity values Ri and is as defined in formula (II):

$$\text{mean} = \frac{1}{n}\sum_{i=1}^{n} Ri. \quad \text{(II)}$$

Preferably, said rigidity values Ri follow at ±10%, in particular at ±5%, preferably at ±1%, a symmetrical distribution, provided that the mean "mean" and the median "median" of said distribution are such that the deviation e defined in formula (III):

$$e = 2\frac{\text{mean} - \text{median}}{\text{mean} + \text{median}} \quad \text{(III)}$$

is less than 10%, in particular less than 5%, preferably less than 1%. The standard deviation a of the rigidity values is then as defined above, or not.

The median is the "median" rigidity value which makes it possible to divide the series of n ordered rigidity values Ri into two parts with the same number of elements. The set of rigidity values Ri is then cut into two parts having the same number of elements: with on one side half of the rigidity values Ri, which are all less than or equal to "median" and on the other side the other half of the rigidity values Ri, which are all greater than or equal to "median".

The lower the value e, the more the rigidity values Ri follow a symmetrical distribution. A perfectly symmetrical rigidity distribution has a deviation e of 0.

Preferably, said rigidity values Ri follow at ±10%, in particular at ±5%, preferably at ±1%, a normal distribution, provided that the mean "mean" and the median "median" of said distribution are such that the difference e is less than 10%, in particular less than 5%, preferably less than 1%.

Preferably, the n points are distributed randomly over the entire surface of the gel.

Preferably, the variability of its rigidity at the micrometer scale is less than 10%, preferably less than 5%. The rigidity is measured at the surface of the gel on which the nano-objects will be deposited in step b). In other words, the difference in rigidity of two points of the gel separated by 1 µm preferably does not exceed 10%.

Preferably, the variability of the rigidity of the gel on a centimeter scale is less than 20%, in particular less than 15%, preferably less than 10%.

Particularly preferably, the variability of the rigidity of the gel is less than 20%, in particular less than 15%, preferably less than 10%. In other words, the difference in rigidity of two points (wherever they are on the surface of the gel on which the nano-objects will be deposited during step b)) does not exceed 20%, in particular 15%, preferably 10%.

The gel typically has a surface area greater than or equal to 1 µm², preferably greater than or equal to 10 µm². Areas of less than 1 µm² make it more difficult to measure rigidity variability. Surfaces smaller than 10 µm² make it more difficult to measure a variability in the surface density of nano-objects when the size of these is from 500 nm to 1000 nm. In addition, the surface of the gel is generally less than or equal to 1000 mm². For the surface distribution of nano-objects to be uniform, it is In fact preferable to limit the impact of capillary forces at the interface between the gel, the drop of evaporating solvent and the gas used to evaporate. These capillary forces, in fact, tend to pull the nano-objects towards the center of the drop, and induce a concentration gradient from the edges towards the center. This effect may be observed when the gel surface exceeds 1000 mm$^2$.

The larger the surface of the gel, the easier it is to measure the rigidity at a large number of points. Generally, the smaller the gel surface, the smaller is the deviation e.

When the surface of the gel is less than 80 mm$^2$ (if the surface is circular, its diameter is then less than 10 mm), the distribution is measured over at least 50 points, preferably over at least 500 points, while the deviation e is preferably less than 5%, or even less than 1%.

When the surface of the gel is from 80 mm$^2$ to 1000 mm$^2$ (if the surface is circular, its diameter is then from 10 mm to 35 mm), the distribution is preferably measured over at least 100 points, in particular at least 1000 points, ideally at least 10,000 points, while the difference e is preferably less than 10%, or even less than 5%.

The rigidity of the gel is generally from 0.01 kPa to 500 kPa, in particular from 0.05 kPa to 100 kPa, preferably from 0.1 kPa to 50 kPa.

The local rigidity and, therefore, the variability of rigidity may be determined by Atomic Force Microscopy (AFM), for example by following the protocol described on pages 29 and 30 of application WO 2013/079231.

The method comprises a step b) of depositing nano-objects on the surface of the gel. The nano-objects are preferably chosen from among:
 proteins, peptides and their mixtures,
 polysaccharides, and
 nanoparticles, in particular metal, semiconductor or polymer nanoparticles.

Nano-objects may be bacteria.

Nano-objects are generally not cells. In one embodiment, the nano-objects are not living organisms.

The metal is, in particular, chosen from among alkali metals, alkaline earth metals, lanthanides, actinides, transition metals and so-called "poor" metals, and is preferably chosen from among gold, silver and indium.

The semiconductor is for example cadmium telluride (CdTe).

The polymer nanoparticles may, for example, be made of polystyrene or of latex.

The proteins, peptides, polysaccharides and mixtures thereof are the preferred nano-objects, in particular proteins and/or peptides inducing cell adhesion via integrins, such a protein possibly being fibronectin, fibrinogen, collagen or laminin, vitronectin or peptides of the RGD type. The proteins and/or the peptides and/or the polysaccharides may have been modified so that they carry a function capable of reacting with the polymer matrix of the gel.

The prefix "nano" means that the average diameter of the nano-object lies between 1 and 1000 nm, in particular between 2 to 500 nm, for example between 2 to 250 nm. Gold nanoparticles typically have average diameters of 5 to 400 nm. Silver or indium nanoparticles typically have average diameters of 2 to 10 nm.

The nano-objects deposited in step b) have an average diameter greater than or equal to the average diameter of the pores of the gel (average diameter of the pores when the nano-objects are deposited, i.e. under the conditions of step b)). This allows the nano-objects to remain on the surface of the gel and not sink, or only slightly, into the polymer matrix. In fact, if the nano-objects can penetrate within the gel in a significant proportion, then the surface density of the nano-objects deposited on the surface of the desolvated gel is all the greater as the pores are small. In this case, the surface density of the nano-objects is not independent of the rigidity/porosity of the gel.

Preferably, the nano-objects deposited in step b) have an average diameter at least two times greater, in particular at least three times greater, in particular at least four times greater, preferably at least five times greater, for example at least ten times greater, than the average pore diameter of the gel.

The average pore diameter of the gel may be measured by neutron or small angle x-ray scattering. It is typically in the range of 2 to 4 angstroms.

The average diameter of proteins or peptides is typically measured by gel electrophoresis. The average diameter of polysaccharides is generally measured by High Pressure Liquid Chromatography (HPLC), coupled with light scattering (which makes it possible to determine the hydrodynamic radius). The average diameter of the nanoparticles is typically measured by Transmission Electron Microscopy (TEM) and Scanning Electron Microscopy (SEM).

Generally, during step b), the nano-objects are deposited in the form of a mixture comprising the nano-objects and a solvent. The solvent for this mixture may be the same or different from the solvent of the gel. Preferably, the solvent of the mixture is soluble in the solvent of the gel (soluble under the conditions of step b)). Preferably, the solvent of the mixture is identical to the solvent of the gel.

The mixture may be colloidal (the nano-objects being in suspension).

The method may comprise, between steps b) and c), a step b1) consisting in leaving the nano-objects in contact on the surface of the gel, generally for a period of 1 min to 24 hours, in particular 1 min to 12 hours, by example 5 min to 1 hour. When the nano-objects are proteins, this step corresponds to an incubation.

The method is preferably free, between steps b) and c):
 of a step consisting in removing part of the nano-objects from the surface of the gel, for example carried out by aspirating the supernatant solution from above the surface of the gel, and/or
 of a rinsing step.

In fact, it is more difficult to control the quantity of remaining nano-objects, and therefore the surface density of nano-objects of the gel obtained, when such steps are carried out.

The method comprises a step c) of evaporating the solvent from the gel at least until the solvent content no longer varies over time.

Figure 1:
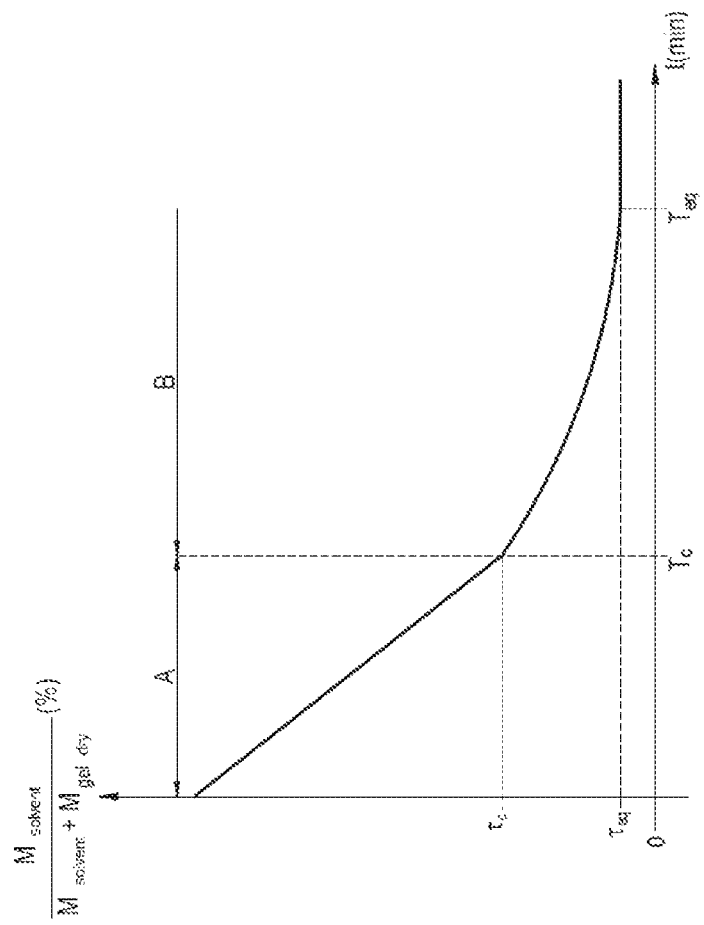
FIG. 1 is a graphic representation of the first and second period of evaporation using a gel of the present disclosure wherein solvent content beyond the equilibrium time $T_{eq}$ is non-zero.
Figure 2:
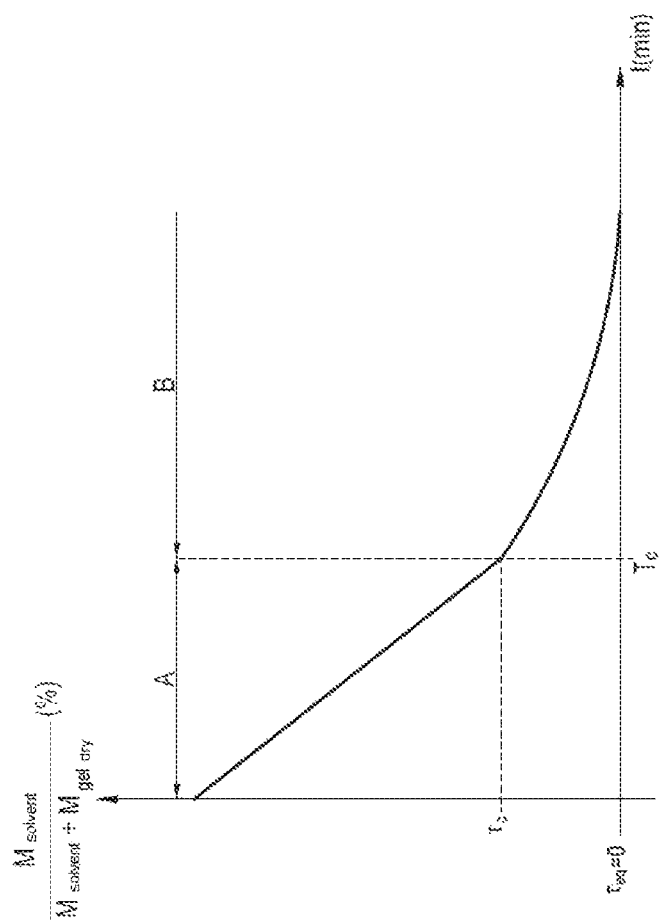
FIG. 2 is a graphic representation of the first and second period of evaporation using a gel of the present disclosure wherein solvent content beyond the equilibrium time $T_{eq}$ is zero.

Evaporation of the solvent from a gel of uniform density comprises two regimes which are illustrated in FIGS. 1 and 2.

During the first period of evaporation ("A" in FIGS. 1 and 2), solvent is continuously removed from the gel surface by capillary forces, while the solvent content decreases at a constant rate, which is explained by the fact that the surface of the gel is sufficiently wetted by the solvent and behaves like the surface of a liquid. Its evaporation rate is equal to that of a liquid surface, which depends only on the gas used for drying and the transfer coefficient of the boundary layer of the gel surface.

When evaporation is continued, the evaporation rate reaches a critical evaporation rate at a critical evaporation time $T_c$ which marks the transition between the first and second evaporation periods.

During the second period of evaporation ("B" in FIGS. 1 and 2), the diffusion forces become predominant over the capillary forces and the removal of the solvent from the gel is mainly controlled by the diffusion of the solvent into the pores of the gel towards its surface. The rate of evaporation of the solvent is not constant over time. It decreases until it reaches an equilibrium evaporation rate at an equilibrium time $T_{eq}$ beyond which the gel can no longer be dried, i.e. the solvent content no longer varies over time.

In step c) of the method according to the invention, the evaporation of the solvent is carried out at least up to this equilibrium time $T_{eq}$, which is the minimum time from which the solvent content no longer varies over time.

The solvent content beyond the equilibrium time $T_{eq}$ may be non-zero (FIG. 1) or zero (FIG. 2), depending on the gel and the solvent used. For example, for a hydrogel (for which the solvent is an aqueous solution), the solvent content beyond the equilibrium time $T_{eq}$ of a hygroscopic polymer matrix will be non-zero, whereas the solvent content beyond the equilibrium time $T_{eq}$ of a non-hygroscopic polymer matrix will be zero.

The equilibrium time $T_{eq}$ is a characteristic of each gel. It depends on the nature of the solvent and on the nature of the polymer matrix (i.e. on the nature of the polymer, but also on its porosity and therefore on its rigidity), and on the conditions of step c).

When the solvent is an aqueous solution (the gel then being a hydrogel), the evaporation of the solvent is a dehydration.

Usually, in step c):
evaporation is carried out by bringing the gel into contact with a gas which is air or an inert gas (such as nitrogen or argon), preferably air, and/or
the pressure is 0.1 to 1 bar, preferably 1 bar, and/or
the temperature of the gas brought into contact with the gel is from 4 to 90° C., in particular from 10 to 70° C., preferably from 15 to 40° C., in particular at room temperature (20° C.) or at 37° C., and/or
the speed of the gas brought into contact is between 0 and 4 m/s, in particular from 0 to 1 m/s, preferably of the order of 0.45 m/s to 0.50 m/s (for example when the gel is placed under a laminar flow hood),
these conditions being independently constant over time or variable over time during step c).

Of course, the higher the temperature and/or the higher the speed of the gas contacted, the faster will be the evaporation of the solvent, and therefore step c). When the nano-objects have an average diameter at least ten times greater than that of the average diameter of the gel pores, the acceleration of evaporation does not impact the distribution of the nano-objects on the surface of the gel, because they do not penetrate within the gel. However, when the nano-objects have an average diameter of the same order of magnitude as that of the average pore diameter of the gel, the acceleration of evaporation helps limit the penetration of the nano-objects into the gel. Higher temperatures and/or a higher speed of the gas contacted are then to be preferred.

The temperatures and speed of the gas must not, however, be too high to avoid degrading the gel and/or the nano-objects (for example, certain proteins degrade beyond certain temperatures, or a gas projected at too high a speed may damage the gel surface and/or lead to its fracturing/cracking).

Preferably, at least until the equilibrium time $T_{eq}$, or even during the duration of step c), the evaporation conditions are constant over time, i.e.:
when the evaporation is carried out by bringing the gel into contact with a gas:
the nature of the gas remains the same over time,
the gas flow rate is constant at ±10%, and
the gas temperature is constant at ±2° C., and
the (de)pressurization is constant at ±10% over time (where (de)pressurization means pressurization (P1 bar)) or depressurization (P<1 bar), for evaporation under vacuum for example).

Generally, in order to allow evaporation of the solvent during step c), at the start of step c) (when the evaporation has started), the gel has a solvent content $T_d$ greater than the solvent content $T_{eq}$ of the gel at equilibrium time $T_{eq}$. In practice, this condition is almost always true when the nano-objects are deposited as a mixture comprising the nano-objects and a solvent.

During step c), at the start of evaporation, the content of mineral salts in the solvent is less than 6 g/l, in particular less than 5 g/l, typically less than 4 g/l, for example less than 3 g/l, preferably less than 2 g/l, wherein a content of less than 1.5 g/l, or even less than 1.0 g/l, or even less than 0.5 g/l, is particularly preferred. Preferably, during step c), the solvent is free from inorganic salts.

Chloride salts (NaCl, KCl, $CaCl_2$ and/or $MgCl_2$), phosphate salts ($Na_2HPO_4$ and/or $K_2HPO_4$), carbonate salts ($NaHCO_3$) are examples of inorganic salts. These are used in the usual way in physiological aqueous and/or buffer solutions used as a solvent in hydrogels and for proteins.

Generally, the users know the mineral salt content at the start of evaporation, because they know the mineral salt content in the gel supplied in step a), as well as the content of mineral salts possibly added during step b), (these mineral salts may, in particular, come from the solvent of the mixture comprising the nano-objects and a solvent deposited during step b)). If the mineral salt content is unknown, it may be determined by ion chromatography.

The invention is based on the discovery that the total evaporation of the solvent from the gel (i.e. at least until the solvent content no longer varies over time) makes it possible to easily control the surface distribution of the nano-objects and therefore their surface density, without degrading either the gel or the nano-objects. As the solvent is evaporated, it is easy to know the quantity of nano-objects deposited on the surface of the gel, since this quantity corresponds to the quantity of nano-objects deposited during step b), (provided that some of the nano-objects have not been removed between steps b) and c) (by aspiration of the solution or by rinsing)). The surface density of deposited nano-objects is therefore known with great precision. During step c), the nano-objects are deposited without limit due to the diffusion of the nano-objects towards the surface of the gel.

There was a technical prejudice to overcome in order to implement the method according to the invention. In fact, those skilled in the art completely avoid evaporating the solvent from the gel, because they expect its degradation, in particular by cracking/fracturing and depositing crystals. However, these degradations are observed only when the mineral salt content exceeds that mentioned above. Without wishing to be bound by a particular theory, the inventors note that the mineral salts present at higher contents, crystallize during the evaporation of the solvent, which leads to cracking of the gel, in particular during its re-swelling with a view to its use in solvated form, wherein this, in general, leads to the presence of numerous deposits and irremovable crystals on the surface. Preferably, during step c), the solvent is free from a compound capable of crystallizing under the conditions of step c).

Additional technical prejudices existed where nano-objects are proteins. In fact, those skilled in the art generally avoid completely evaporating the solvent from the gel, as they expect the proteins to degrade if they run dry. This is because most protein suppliers recommend that we avoid drying a protein that has been dissolved in order to avoid denaturing it. However, surprisingly, such denaturation is generally not observed in the method according to the invention. In addition, those skilled in the art are accustomed to using proteins in physiological media, which are aqueous solutions that are usually buffered, and whose content of inorganic salts exceeds that mentioned above. Using a solvent so the salt content is as defined in step c) is very unusual for those skilled in the art.

Advantageously, the surface density of nano-objects on the gel obtained at the end of step c) is independent of the rigidity of the gel used. The rigidity of the gel only affects the kinetics of evaporation (over time to reach the equilibrium time $T_{eq}$).

Advantageously, the surface density of nano-objects of the gel obtained in step c) is uniform.

The method for measuring the surface density of nano-objects varies according to the nature of the nano-objects. For example, when the nano-objects are proteins, we may use a primary antibody capable of recognizing said protein, then a secondary antibody capable of recognizing said primary antibody, this secondary antibody being bound to a fluorophore, then analyzing the surface density by confocal fluorescence microscopy. When the nano-objects are nanoparticles, the surface density may be analyzed by scanning electron microscopy.

The method may include, before step a), the steps of:

a0) providing a gel having an initial solvent content $\tau_i$ greater than the solvent content $t_a$, then a0') evaporating the solvent from the gel to the initial solvent content $t_a$, whereby a gel as defined in step a) is obtained.

The evaporation of step a0') is therefore carried out before the deposition of the nano-objects. This prior evaporation makes it possible to reduce the thickness of the solvent layer on the surface of the gel and thus to promote the migration by convection of the nano-objects towards the surface of the gel during step b) which follows.

The method may comprise, before step b), a step b0) consisting in grafting to the surface of the gel functional groups capable of reacting with the nano-objects which will be deposited in step b).

The nano-objects deposited during step b) may have been modified before step b) so that they carry a function capable of reacting with the polymer matrix of the gel. The method may comprise, before step b), a step b0') consisting in grafting onto the nano-objects (in particular the proteins and/or the peptides and/or the polysaccharides) at least one functional group capable of reacting with the gel.

In steps b0) and b0'), the functional groups are preferably capable of reacting to form a covalent bond.

When the nano-objects are proteins and/or peptides and/or polysaccharides, the method may comprise a step d) of covalent grafting of the proteins and/or peptides and/or polysaccharides on the gel, which makes it possible to immobilize them definitively and to prevent the peptides and/or proteins and/or polysaccharides from moving again on the surface of the gel, during rinsing of the gel after step c) for example. This step d) may be simultaneous with step c) (during evaporation), or may be carried out after step c) (on the desolvated gel). Preferably, when step d) is carried out, the method does not include a rinsing step between steps a) and d).

The method may comprise, after step c), a step e) of rinsing with a solvent. This solvent may be the same or different from the gel solvent. The rinsing step may be repeated.

The method may comprise, after step c), or, if present, after step e), a step f) of recovering the gel. The gel is in desolvated form (solvent content beyond the equilibrium time of the gel) if it is recovered at the end of step c). If a rinsing step e) is carried out after step c) and before step f), the gel may be in solvated form (the solvent being the solvent of the rinsing solution). The gel in solvated or desolvated form may advantageously be stored for several months, generally at least one month, in particular at least three months, or even at least nine months at room temperature (20° C.), generally without any degradation either of the gel or of the nano-objects (including no denaturation of proteins) being observed.

The method according to the invention is easy to implement. It does not require complex equipment. It is inexpensive.

According to a second object, the invention relates to the gel capable of being obtained by the method defined above, the surface of the gel being at least partially coated with nano-objects, where the standard deviation σ' of the quantities Qj (j varying from 1 to p) of nano-objects per µm² of area is less than 40%, typically less than 30%, in particular less than 20%, preferably less than 10%, the quantities Qj of nano-objects being measured by microscopy over p µm² of surface distributed over the entire surface of the gel, p being greater than 10, in particular greater than 100, typically greater than 10,000 (100×100), preferably greater than 1,000,000 (1,000×1,000), the standard deviation σ' being as defined in formula (IV):

$$\sigma' = \sqrt{\frac{1}{p}\sum_{j=1}^{p} (Qj - \text{mean}')^2} \quad \text{(IV)}$$

where "mean" is the arithmetic mean of the quantities Qj of nano-objects per µm² of area and is as defined in formula (V):

$$\text{mean}' = \frac{1}{p}\sum_{j=1}^{p} Qj. \quad \text{(V)}$$

Preferably, said quantities Qj of nano-objects per µm² of surface area follow at ±10%, in particular at ±5%, preferably at ±1%, a symmetrical distribution, provided that the arithmetic mean "mean" and the median "median" of said distribution are such that the difference e' as defined in formula (VI):

$$e' = 2\frac{\text{mean}' - \text{median}'}{\text{mean}' + \text{median}'} \quad \text{(VI)}$$

is less than 25%, in particular less than 20%, typically less than 10%, preferably less than 5%. The standard deviation a' of the quantities Qj (j varying from 1 to p) of nano-objects per µm² of surface is then as defined above, or not.

The median is the "median'" quantity of nano-objects per µm² of surface area which makes it possible to divide the series of p quantities of nano-objects per µm² of surface ordered into two parts with the same number of elements. The set of quantities Qj of nano-objects per µm² of area is then cut into two parts having the same number of elements: with, on the one hand, half of the quantities Qj of nano-objects per µm² of area, which are all less than or equal to "median'" while, on the other hand, the other half of the values of quantities Qj of nano-objects per µm² of surface, are all greater than or equal to "median'".

The lower the e' value, the more the quantities Qj of nano-objects per µm² of surface follow a symmetrical distribution. A perfectly symmetrical surface distribution in nano-objects has a deviation e' of 0.

Preferably, said quantities Qj of nano-objects per µm² of surface area follow at ±10%, in particular at ±5%, preferably at ±1%, a normal distribution, provided that the mean "mean'" and the median "median'" of said distribution are such that the difference e' is less than 25%, in particular less than 20%, typically less than 10%, preferably less than 5%.

Preferably, the p µm² of surface are distributed randomly over the entire surface of the gel.

Preferably, the variability of the surface density of nano-objects at the surface of the gel is less than 60%, in particular less than 50%, typically less than 40%, preferably less than 30%.

Generally, the gel, solvated or unsolvated, is not cracked, and may be characterized as follows:
optically, in phase contrast microscopy,
by measuring the rigidity: by scanning a surface, force/indentation curves are observed which are not elastic at the level of the fractures (presence of breaks in the curve for low amplitude indentations).
or electron microscopy, if the sample is not transparent.

This gel has very variable applications depending on the nature of the nano-objects deposited on the surface. According to a third object, the invention relates to the use of this gel for cell culture, for the screening of active pharmaceutical ingredients, as a photonic sensor (typically when the nano-objects are semiconductors) or physicochemical, for example as a sensor of pH (typically when the nano-objects are gold particles), or temperature (typically when the nano-objects are CdTe particles), as a sensor for analyte detection, as a protein or peptide chip (typically when the nano-objects are proteins and/or peptides), as cell chips or as biomolecule capture chip.

The invention also relates to:
a cell positioning method for screening active pharmaceutical ingredients comprising bringing pharmaceutical active ingredients into contact with the gel according to the invention, in which the nano-objects are peptides, proteins and/or polysaccharides,
a method for capturing biomolecules comprising bringing into contact a medium comprising biomolecules to be captured with the gel according to the invention in which the nano-objects are peptides, proteins and/or polysaccharides,
an analysis method comprising bringing a medium comprising an analyte to be detected into contact with the gel according to the invention.

The figures and examples below illustrate the invention.

The examples were carried out with polyacrylamide hydrogels and proteins (fibronectin or fibrinogen) as nano-objects.

The polyacrylamide hydrogels used had a rigidity variability of 10% at the centimeter scale and 5% at the 100 µm scale (a rigidity measurement was taken every 10 µm).

EXAMPLE 1

Grafting of Previously Activated Proteins (Fibronectin) on the Surface of Polyacrylamide Hydrogels In this example, a photosensitive crosslinker was grafted to the fibronectin used as protein, to make it reactive with the surface of the hydrogel under exposure to UV A. The grafting of the fibronectin previously activated on the surface of the gel is a photoactivated reaction.

a) Silanization of Basal Glass Coverslips

The basal coverslip serves as the basal anchor for the hydrogel.

The basal glass coverslip, with a diameter of 30 mm, was cleaned in a solution of 0.1 mol/L of sodium hydroxide for 10 min. It was then rinsed extensively with water, then with ethanol, and air dried.

500 µL of a silane solution comprising 56 µL of Bind-Silane (GE Healthcare), 484 µL of 10% acetic acid, and 14.46 mL of ultra pure ethanol were placed on the coverslip and rubbed with a knitted polyester cloth until all traces of solution disappear. A glass slide was thus obtained having aldehyde functions at its surface, which allow covalent grafting of the polyacrylamide gel.

b) Silanization of the Transparent Mask

The hydrogel is crosslinked by UV, the transparent mask allowing the surface of the hydrogel to be flat. The mask consisted of a microscope coverslip treated with a fluorinated silane to limit its adhesion to the hydrogel.

An optical microscopy coverslip (26 mm×76 mm) was washed in a 1:2 concentrated hydrogen peroxide/sulfuric acid solution for 10 minutes. It was then made hydrophobic by an Optool treatment (Daikin DSX): immersion for 1 minute in Optool diluted to 1/1000 in perfluorohexane. Then the coverslip was left for 1 hour in water vapor at 80° C. Finally, it was immersed with slow stirring for 10 minutes in perfluorohexane.

c) Preparation of Three Polyacrylamide Hydrogels

The hydrogel was prepared according to the method described in application WO 2013/079231 from a composition consisting of:
10% acrylamide (250 µL of initially 40% solution)
0.5% of N, N'-methylenebisacrylamide (Bis) (250 µL of initially 2% solution)
0.2% of Irgacure 819 w/v (Ciba, photoinitiator)
1% propylamine (initiator)
deionized water (490 µl)

Irgacure 819 was weighed in a UV-opaque bottle. Propylamine was added to it. The whole was heated at 50° C. for 2 minutes. After heating, a homogeneous and transparent solution was obtained. Water, acrylamide, and bis acrylamide were added quickly. The whole was homogenized gently with a pipette, to limit the incorporation of oxygen. 30 µL were deposited on the 30 mm glass coverslip pretreated according to the above protocol. The coverslip was placed on a sample holder having spacers which maintain a spacing of 40 µm between the coverslip and the transparent mask, deposited on the spacers. The whole (mask, solution, coverslip) was illuminated using an Eleco UVP281 fiber lamp (2 W/cm²) for 7.8 s, 15 s or 20 s, in order to obtain three hydrogels. Each set was then immersed in water to detach the mask from the hydrogel using forceps. Each hydrogel was rinsed 3 times with deionized water and stored in deionized water.

d) Characterization of the Rigidity of Hydrogels

The variability in porosity of each hydrogel was estimated by measuring the local rigidity of the hydrogel. The local rigidity was measured by an AFM in aqueous medium (JPK brand). The resistance of the gel to the indentation of the point was recorded. Four 100 µm×100 µm regions spaced several millimeters apart were scanned. The scans were performed with a step of 10 µm in order to obtain a series of indentation curves. Each curve was processed according to the manufacturer's protocol with an elastic indentation model.

The rigidities obtained are dependent on the illumination time to prepare the gel. They are of the order:

0.6 kPa with a standard deviation a of the rigidity values Ri of 11.7% for a hydrogel prepared with an illumination time of 7.8 s, 11.8 kPa with a standard deviation a of the rigidity values Ri of 11.8% for a hydrogel prepared with an illumination time of 15 s and 24.7 kPa with a standard deviation a of the rigidity values Ri of 9.2% for a hydrogel prepared with an illumination time of 20 s.

e) Deposition of Activated Fibronectin on the Hydrogel Followed by Covalent Grafting The fibronectin was previously coupled to the heterobifunctional sulfo-NHS-LC-Diazirine (Sulfosuccinimidyl-6-(4,4'-azipentanamido) hexanoate crosslinker, ThermoScientific Pierce; trade name: sulfo-LC-SDA), with a molar ratio of 1/480.5 mg of fibronectin (Roche) was dissolved in 2 mL of ultrapure deionized water, at 37° C. for 30 min. 1.2 mg of sulfo-LC-SDA were weighed in the dark and dissolved in the fibronectin solution for 30 min at room temperature. This operation was repeated a second time, resulting in the molar ratio of 1/480. This protocol made it possible to react the sulfo-NHS function of the sulfo-LC-SDA with the amine groups of the fibronectin while limiting the hydrolysis of the sulfo-LC-SDA. The compound formed is a fibronectin molecule coupled to a photosensitive diazirine function. The compound formed was dialyzed through a 6-8000 membrane in a dark room and at 4° C. against 2 l of PBS +/+ 1 × for 48 h with a change of PBS after 24 h. It was then aliquoted in small volumes (25 and 50 µl) and stored frozen at −20° C.

The hydrogel prepared according to the above protocol was dehydrated under a vertical laminar flow hood (Aura) at 26° C. for one hour (step a0')).

In a room with UV-free lighting, 800 µl of conjugated fibronectin solution according to the above protocol was prepared at a concentration of 3.5 µg/ml in sterile deionized water, and was deposited using with a pipette on the gel (step b)).

The whole hydrogel+fibronectin solution was placed on a hot plate at 37° C. under a laminar flow hood (convective flow of 0.5 m/s) until the solution had completely evaporated from the surface of the hydrogel (step c)).

The gel was immediately illuminated by the ElecoUVP281 UV lamp for 5 min (step d)). It was then gently rinsed 3 times with a solution of PBS +/+ (steps e)). The functionalized gel was stored hydrated in a solution of PBS +/+, at 4° C.

f) Characterization of the Distribution of Grafted Proteins

The PBS +/+ solution was aspirated from the gel, and replaced with a saturation solution consisting of a solution of PBS +/+ 1×-0.1% Tween20-2% BSA, for 30 min with slow stirring at room temperature.

The saturation solution was aspirated using a pipette and replaced by a solution of 3 µL of primary polyclonal anti fibronectin antibody produced in rabbits (Sigma-Aldrich, F3648) diluted in 1.2 mL of PBS +/+ 1×-0.1% Tween20-2% BSA. The antibody was incubated for 1 hour with slow stirring at room temperature. It was then revealed with 1.2 mL of a solution containing 0.6 µL of a secondary antibody coupled to Alexa 488 produced in the donkey and directed against the rabbit (Molecular Probes, A21206), supplemented by a 1x PBS +/+ solution-0.1% Tween20 -2% BSA for 1 hour with slow stirring at room temperature and protected from light. The solution was then removed by aspiration and the gel was rinsed 3 times with 1.2 mL of PBS +/+ 1×-Tween20 0.1%-BSA 2%. The gel was then stored in a solution of PBS +/+ 1×at 4° C. and protected from light.

The characterization of the distribution of the grafted proteins was carried out by confocal fluorescence microscopy (Leica SP microscope). An image stack was acquired for each hydrogel at the wavelength 488 nm with an image spacing of 0.28 µm. The various acquisitions were made at constant gain and at constant laser intensity. Each stack of images was then assembled with ImageJ software and sections were extracted. The maximum intensity image was calculated from the image stack, resulting in a two-dimensional projection of the fluorescent surface for 375×375 µm windows. The antibody markings lead to obtaining pixelated images. To remedy this, the pixelation was limited by a Gaussian filter with a radius of 10 pixels. Then the mean value of the intensity was calculated on this projection (Table 1).

TABLE 1

Average fluorescence intensity over an area of 375 × 375 µm² and variability of the protein surface density for each hydrogel.

| | 0.6 kPa rigidity gel | 11.8 kPa rigidity gel | 24.7 kPa rigidity gel |
|---|---|---|---|
| Average fluorescence intensity | 85.1 ± 13.5 | 81.1 ± 10.5 | 80.7 ± 19.8 |
| Standard deviation σ' of the quantities Qj of proteins per µm² of surface area | 16% | 13% | 25% |

The lack of significant variation in intensity between each of the three hydrogels demonstrates that the amount of grafted protein is independent of the rigidity/porosity of the hydrogel.

EXAMPLE 2

Grafting of Proteins (Fibrinogen) on the Previously Activated Surface of a Polyacrylamide Hydrogel In this example, the same crosslinker as that of Example 1 was attached in excess to the surface of the hydrogel by photochemical reaction to obtain an activated surface, wherein the proteins (fibrinogen) reacted with the activated surface of the hydrogel by a coupling reaction with the primary amine functions of the proteins.

a) Silanization of Basal Glass Coverslips

Same as Example 1a.

b) Silanization of the Transparent Mask

Same as Example 1b.

c) Preparation of Three Hydrogels

Same as Example 1c. The illumination times were 7.5, 9, and 10 s.

d) Characterization of the Rigidity of each Hydrogel

Same as Example 1d. The rigidities obtained were respectively:

2.9 kPa with a standard deviation σ of the rigidity values Ri of 10.3%, 4.6 kPa with a standard deviation σ of the rigidity values Ri of 4.3% and 9.5 kPa with a standard deviation σ of the rigidity values Ri of 9.5%.

e) Activation of the Surface of the Hydrogels (Step b0))

In a room with UV-free lighting, each hydrogel prepared according to the above protocol was dehydrated in a vertical laminar flow hood (Aura) at 26° C. for one hour. A solution of the hetero-bifunctional sulfo-NHSLC-Diazirine (Sulfosuccinimidyl 6-(4,4'-azipentanamido) hexanoate, Thermo-Scientific Pierce; trade name: sulfo-LC-SDA) crosslinker was prepared in sterile deionized water at a concentration of 0.44 mg/mL. 800 µl of this solution were deposited on the gel using a pipette. This solution was allowed to incubate for 60 min at 26° C. under the laminar flow hood. The residual solution was then gently aspirated with a pipette, and the gel was again allowed to dry for 40 min, still under the laminar flow hood.

The gel was then illuminated by the ElecoUVP281 UV lamp for 5 min.

f) Covalent Grafting of Fibrinogen

A solution of fibrinogen coupled to a fluorescent Alexa Fluor 488 probe (F13191, Invitrogen) was prepared at a concentration of 8.75 µg/mL. 800 µl of this solution were deposited on the activated surface of the gel using a pipette (step b)).

The hydrogel+fibrinogen solution assembly was placed on a hot plate at 37° C. under a laminar flow hood (convective flow of 0.5 m/s) until complete evaporation of the solution on the surface of the hydrogel (steps c) and d)).

The gel was then gently rinsed 3 times with a solution of PBS +/+ (steps e)). The functionalized gel was stored hydrated in a solution of PBS +/+, at 4° C. and protected from light.

g) Characterization of the Distribution of Grafted Proteins

The grafted proteins were coupled to a fluorophore. The characterization of the distribution of the grafted proteins was carried out by confocal fluorescence microscopy (Leica SP microscope). An image stack was acquired for each rigidity step at the wavelength 488 nm with an image spacing of 0.28 µm. The various acquisitions were made at constant gain and at constant laser intensity. Each stack of images was then assembled with ImageJ software. The maximum intensity image was calculated from the image stack, resulting in a two-dimensional projection of the fluorescent surface. The antibody markings lead to obtaining pixelated images. To remedy this, the pixelation was limited by a Gaussian filter with a radius of 10 pixels. Then the mean value of the intensity was calculated on this projection (Table 2).

TABLE 2

Average fluorescence intensity over an area of 375 × 375 µm² and variability of the protein surface density for each hydrogel.

| | 2.9 kPa rigidity gel | 4.6 kPa rigidity gel | 9.5 kPa rigidity gel |
|---|---|---|---|
| Average fluorescence intensity | 178.4 ± 49.5 | 167.5 ± 48.7 | 144.9 ± 40.6 |
| Standard deviation σ' of the quantities Qj of proteins per µm² of surface area | 28% | 29% | 28% |

The lack of significant variation in intensity between each of the three hydrogels demonstrates that the amount of grafted protein is independent of the rigidity/porosity of the hydrogel.

The invention claimed is:

1. A method of depositing nano-objects on the surface of a gel with uniform rigidity, said method comprising:

a) providing a gel comprising a polymer matrix and a solvent within the polymer matrix, the polymer matrix forming a three-dimensional network capable of swelling in the presence of said solvent, where the solubility of the polymer matrix at 1 bar and 25° C. in the solvent is less than 1 g/l, and having rigidity values measured by atomic force microscopy on n points distributed over the entire surface of the gel that follow ±10% a symmetrical distribution, provided that the arithmetic mean and median of said distribution have a deviation e as defined in formula (III):

$$e = 2\frac{\text{mean} - \text{median}}{\text{mean} + \text{median}} \quad \text{(III)}$$

wherein e is less than 10% and is measured by atomic force microscopy, the variability of the rigidity value at the centimeter scale being less than 20%, then b) depositing nano-objects on the surface of the gel, said nano-objects having an average diameter greater than or equal to the average diameter of the pores of the gel, then c) evaporating the solvent from the gel at least until it reaches an equilibrium evaporation rate at an equilibrium time $T_{eq}$ beyond which the gel can no longer be dried, said rate of evaporation of the solvent decreasing until is reaches said equilibrium evaporation rate, provided that at the start of evaporation the content of inorganic salts in the solvent is less than 6 g/l.

2. The method according to claim 1, wherein said rigidity values follow ±10% a symmetrical distribution, provided that the arithmetic mean and the median of said distribution are such that the deviation e as defined in formula (III):

$$e = 2\frac{\text{mean} - \text{median}}{\text{mean} + \text{median}} \quad \text{(III)}$$

is less than 10%.

3. The method according to claim 1, wherein the polymer matrix of the gel comprises a polymer selected from the group consisting of:

polyacrylamides;

polyethylene glycols, polypropylene glycols and ethylene glycol or propylene glycol copolymers, these optionally comprising units resulting from the polymerization of (meth)acrylate compounds;

polysaccharides, optionally comprising repeating units resulting from the polymerization of (meth)acrylate compounds;

(co)polymers resulting from the polymerization of diacrylate and/or (meth)acrylate compounds;

polyvinyl alcohols comprising repeating units resulting from the polymerization of (meth)acrylate compounds;

dextrans comprising repeating units resulting from the polymerization of (meth)acrylate compounds;

polypropylene fumarates and poly(propylene fumarate-co-ethylene glycol);

polysiloxanes; and combinations thereof.

4. The method according to claim 1, wherein the solvent present within the polymer matrix of the gel is an aqueous solution.

5. The method according to claim 4, wherein the aqueous solution is water.

6. The method according to claim 1, wherein the solvent present within the polymer matrix of the gel is selected from the group consisting of pentane, triethylamine, diisopropylamine, and xylene, and the polymer matrix comprises poly(dimethylsiloxane).

7. The method according to claim 1, wherein the nano-objects are selected from the group consisting of:
proteins, peptides and mixtures thereof,
polysaccharides, and
nanoparticles.

8. The method according to claim 7, wherein the nano-objects are selected from the group consisting of polysaccharides, proteins, peptides and mixtures thereof.

9. The method according to claim 8, further comprising covalent grafting of proteins and/or peptides and/or polysaccharides on the gel.

10. A gel obtainable by the method according to claim 1, the surface of the gel being at least partially coated with nano-objects, wherein quantities $Q_j$ of nano-objects per $\mu m^2$ -of area, being measured by microscopy over p $\mu m^2$ of surface distributed over the entire surface of the gel, follow at ±10%, a symmetrical distribution, provided that the arithmetic mean and median of said distribution are such that the difference e' as defined in formula (VI):

$$e' = 2\frac{mean' - median'}{mean' + median'} \quad (VI)$$

is less than 25%.

* * * * *